United States Patent [19]

Nambu et al.

[11] Patent Number: 4,916,170

[45] Date of Patent: Apr. 10, 1990

[54] PROCESS FOR MAKING SKIN MARKER

[75] Inventors: Masao Nambu, Yokohama; Nobuichi Makino, Nagoya, both of Japan

[73] Assignee: Nippon Oil Co., Ltd., Tokyo, Japan

[21] Appl. No.: 224,938

[22] Filed: Jul. 27, 1988

Related U.S. Application Data

[63] Continuation of Ser. No. 945,357, Dec. 22, 1986, abandoned.

[30] Foreign Application Priority Data

Dec. 27, 1985 [JP] Japan ................................. 60-292861

[51] Int. Cl.$^4$ ................................................. G21K 1/10
[52] U.S. Cl. ........................................ 523/137; 264/28; 523/307; 524/557
[58] Field of Search ..................... 523/137, 307, 105; 264/28; 524/557

[56] References Cited

U.S. PATENT DOCUMENTS

| 2,378,087 | 6/1945 | Kearney | 128/399 |
|---|---|---|---|
| 3,812,842 | 5/1974 | Rodriguez | 128/659 |
| 4,404,820 | 9/1983 | Romaine | 128/399 |
| 4,506,676 | 3/1985 | Duska | 128/653 |
| 4,528,510 | 7/1985 | Loeffler et al. | 324/309 |
| 4,530,220 | 7/1985 | Nambu et al. | 62/530 |
| 4,583,538 | 4/1986 | Onik et al. | 128/653 |
| 4,604,578 | 8/1986 | Young | 324/307 |
| 4,615,879 | 10/1986 | Runge et al. | 424/9 |
| 4,637,929 | 1/1987 | Quay | 128/653 |
| 4,651,335 | 3/1987 | Kalender et al. | 378/207 |

FOREIGN PATENT DOCUMENTS 48-30463  9/1973  Japan ................................. 523/307

Primary Examiner—Joseph L. Schofer
Assistant Examiner—R. H. Delmendo
Attorney, Agent, or Firm—Majestic, Parsons, Siebert & Hsue

[57] ABSTRACT

A skin marker is provided for diagnosis by X-ray tomography and nuclear magnetic resonance imaging. The skin marker is composed of a vessel in which a non-magnetic and X-ray radioopaque material is dispersed, and a hydrogel of high water content filled in the vessel. The hydrogel is prepared by a process comprising a casting step of casting into the vessel an aqueous solution containing more than 8 wt % and not more than 20 wt % of a polyvinyl alcohol having a degree of hydrolysis of not less than 98 mol % and an average polymerization degree of not less than 1,000, a freezing step of cooling the case aqueous solution to a temperature of not higher than − (minus)n 10° C. to obtain a frozen mass, a thawing step of thawing the frozen mass, and one to seven additional cyclic processing steps each including the freezing and thawing steps.

11 Claims, 1 Drawing Sheet

PROCESS FOR MAKING SKIN MARKER

This is a continuation of application Ser. No. 945,357, filed Dec. 22, 1986, how abandonded.

BACKGROUND OF THE INVENTION

1. Field of Art

The present invention relates to a skin marker for diagnosis both by x-ray tomography and nuclear magnetic resonance imaging. The skin marker is applied on a local point or area on the skin of a patient and then irradiated by X-ray or scanned by electron beam to give image thereof together with the image of the lesion of the patient. Such a skin marker has a utility when used to determine the position of the diseased site by learning the interrelation between the lesion and a certain known point on the skin of the patient of whom the location of the internal diseased portion should be determined prior to radiotherapy or surgical treatment. In determination of the site of the internal lesion, an NMR (nuclear magnetic resonance) tomograph or X-ray tomograph bearing the image of the lesion and the image or images of one or more skin markers is studied to learn the relative position of the lesion while certain points or areas on the skin surface of the patient's body are taken as the standard or reference locations.

2. Related Art Statement

Prior to access to an internal lesion site of a patient for the purpose of inspection or therapeutic treatment, it is essential to learn the precise steric information concerning the lesion site while taking a certain position or positions of the surface of the patient's body as the known or reference position in order to avoid or alleviate damage of normal living tissues at the vicinity of the diseased tissue caused by the surgical or radiotherapeutic treatment and to enhance the effect of such a medical treatment.

The positron emission tomography (PET, PE-CT) and the ultrasonic diagnostic method (US) have been proposed as the measures for observing or inspecting the conditions of the internal living tissues. However, since these methods are inferior in resolution power, reproducibility and signal/noise ratio, the X-ray-CT (Computed or Computerized Tomography) is predominantly used in practical diagnoses. However, the X-ray-CT has the problem that the diagnosis of the tomographical image is disturbed by the presence of images of bones and air (air bubbles in the internal organs and air in trachea) in addition to the hazard of exposure to radioactive X-ray. In order to obviate such problems, it has been tried to adopt the NMR-CT (nuclear magnetic resonance computerized tomography) in practical diagnosis. Although this NMR-CT has a merit that various internal organs and lesion sites are imaged without trespassing thereinto, not all of the lesion sites can be detected by this method. That is, NMR-CT is based on proton density and spin signal relaxation time so that the diseases which do not cause to change these NMR characteristics are not detected. On the other hand, the X-ray-CT is useless for the diagnosis of a morbid state which exhibits no abnormality in response to X-ray irradiation, since it depends on radiolucency of living tissues to X-ray.

Anyway, in consideration of the present status that an almighty or versatile means for imaging and diagnosing the internal organs of human body has not been established, it is desirous that the X-ray-CT and the NMR-CT are used in combination so that their defects are compensated with each other. However, irrespective of either one or both of these methods are employed, the steric information relating to the position of the detected or imaged lesion, particularly the interrelation thereof with a certain known position on the surface of the patient's body, is not directly indicated by any of the known methods.

In the radiotherapy or various surgical treatments and operations, when it is intended to destroy or resect the diseased tissue in a certain internal organ through the surface of skin and the portion vicinal to the diseased tissue of the patient's body, it becomes necessary to learn the precise interrelation between the certain known location or locations on the skin and the lesion site.

Virtually, the only practicable measure to get an information concerning the steric positioning of the lesion site in the living body is to apply at a desired position on the surface of the body of a person who is to be examined, any substance, i.e. a skin marker, which gives a discriminative or distinctive image concurrently with imaging of the internal lesion, and to image the skin marker and the lesion site through a tomographic method so that the steric interrelation between the images is determined. Either in the X-ray computerized tomography or the NMR computerized tomography, use of such a skin marker has already been proposed. In a case where the X-ray-CT is employed, it has been reported that a variety of X-ray radioopaque material may be used. Examples of the most commonly used materials are a copper wire coated with polyethylene and a string-shape solder, these materials being used for their deformability or plastic properties adapted for changing the shapes in conformity with the contour of the surface area onto which they are applied. On the other hand, some plastic tubes are commercially produced and sold as catheters for blood vessel angiography. These tubes are produced by dispersing an X-ray radioopaque material throughout the walls of the tubes, the typical examples of X-ray radioopaque materials used for such purpose being barium sulfate, kaolin, bentonite, talc, aluminum silicate, magnesium silicate, siliceous sand, alumina, illite, vermiculite, nontronite, saponite, chlorite, allophane, calcium phosphate, iodine, iron powder and lead powder. It has been tried that such a tube normally inserted into a blood vessel so as to be imaged by X-ray irradiation is cut to have a desired length and then used as a skin marker. In the X-ray-CT picture, these X-ray radioopaque materials, e.g. plastics materials containing additives which do not pass X-ray, form images clearly discriminated or appreciable as a trace or traces indicating the presence of surface portions. However, these materials cannot be diverted for use as skin markers in the NMR-CT method. In order to mark one or more known positions on the surface of a human body together with the image of the lesion in the NMR imaging, a material emitting clear and intensive NMR signal different from that emitted from the normal skin tissue should be applied on a portion of the surface of the normal skin through which the NMR image is taken. However, since most of the known X-ray radioopaque materials referred to above do not emit NMR signals (proton NMR signals), no NMR-CT image is given thereby similarly to air (air in atmosphere).

Known materials widely used as skin markers for NMR-CT are high water content hydrogels containing water as the main ingredient, and vegetable, animal and silicone oils emitting relatively intense proton signals. However, these materials do not give discriminative images in an X-ray tomograph since they are permissible, in other words, not radioopaque to X-ray. Although it has been tried to admix powders of X-ray radioopaque material, such as barium sulfate or iodine, to one of the skin markers for the NMR-CT, it is difficult to prepare an admixture in which such powders are uniformly dispersed, since they have specific gravity extremely higher than that of water or an oil. The additional demerits caused by inclusion of such an additive are that the density of proton in the NMR-CT skin marker is reduced (due to dilution), and that the relaxation time of proton is seriously lowered, leading to attenuation of the NMR signal.

OBJECTS AND SUMMARY OF THE INVENTION

Accordingly, the object of this invention is to provide a skin marker which can be used both in the NMR diagnosis system and in the X-ray diagnosis system.

More specifically, the object of this invention is to provide a skin marker which emits an NMR signal intensive enough for discrimination from the skin surface of a living body and has a satisfactory impermeability to X-ray, and which has good shape retaining property and may be freely cut into a desired shapes.

A skin marker for diagnosis by X-ray tomography and nuclear magnetic resonance imaging, provided by this invention, comprises a vessel in which a non-magnetic and X-ray radioopaque material is dispersed, and a hydrogel of high water content filled in the vessel, the hydrogel being prepared by a process comprising a casting step of casting into the vessel an aqueous solution containing more than 8 wt % and not more than 20 wt % of a polyvinyl alcohol having a degree of hydrolysis of not less than 98 mol% and an average polymerization degree of not less than 1,000, a freezing step of cooling the cast aqueous solution to a temperature of not higher than −(minus) 10° C. to obtain a frozen mass, a thawing step of thawing the frozen mass, and one to seven additional cyclic processing steps each including the freezing and thawing steps.

DESCRIPTION OF THE INVENTION

Figure 1:
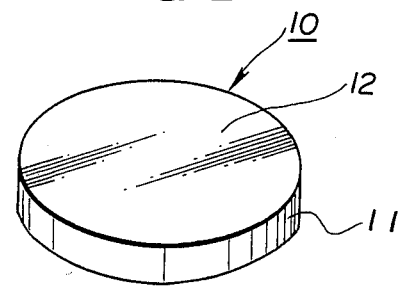
FIG. 1 is a perspective view illustrating a skin marker embodiment as made in Example 1.

The present invention will now be described more specifically hereinbelow.

According to an important aspect of this invention, an X-ray radioopaque and NMR signal emitting skin marker filled with a high water content hydrogel is provided, the hydrogel being prepared through a specific process, as will be described in detail hereinafter and defined in the appended claims.

The polyvinyl alcohol used in the invention should have a degree of hydrolysis of not less than 98 mol %, preferably not less than 98.5%. It is also essential that the polyvinyl alcohol has a degree of polymerization of not less than 1,000.

In the present invention, an aqueous solution containing the aforementioned polyvinyl alcohol is prepared at the first step. The content of the polyvinyl alcohol in the solution should be in the range of more than 8 wt % and not more than 20 wt %, preferably from 9 to 15 wt %

According to another important aspect of this invention, the aforementioned polyvinyl alcohol is cast in a vessel having a desired shape and dimensions and made of a material in which a non-magnetic and X-ray radioopaque material is dispersed. The cast aqueous solution is then cooled and is frozen, followed by thawing to form the high water content hydrogel used in this invention. When it is desired to prepare a skin marker having particularly high mechanical strength, the operation cycle including the freezing and thawing operations may be repeated for additional 1 to 7 times, whereby a rubber-like elastic hydrogel is formed. Although the hardness of the high water content hydrogel is increased with the increase in repeated cyclic treatment, the effect obtainable by the increase in cyclic treatment becomes inappreciable after the ninth cycle (see Masao Nambu, "Polymer Application", 32, 523 (1983)). It is thus recommended, from the economical standpoint of view that the additional cyclic processing is repeated for 1 to 7 times.

The vessel may be in any desired shape, for example, tubular disk, hollow disk or hollow elliptical disk may be used to contain therein the hydrogel. It is also desirous that the vessel be cut into a desired shape and dimensions in compliance with the conditions, including dimensions and shape of the lesion, under which the image of the internal organs is photographed. In view of this requirement, it is preferred that the vessel be made of a material which may be easily cut at the site where actual clinical or inspection action is taken. Examples of preferred materials include synthetic resins, such as polyethylene, polypropylene, polyamides, polyvinylchloride, polyvinylidene chloride, polyesters, polyacrylonitrile, polyfluoroethylene and silicone resins, and natural and synthetic rubbers.

It is also essential that the vessel or container for the hydrogel should be X-ray radioopaque, that is, transmission of X-ray is shielded by the vessel by itself. To satisfy this essential feature, the material for the vessel is dispersed with a contrast medium or shading agent, prior to molding the vessel. In view of the other essential feature that such a material does not hinder the NMR diagnosis, use of magnatic materials, particularly ferromagnetic materials, must be avoided. Accordingly, X-ray radioopaque and non-magnetic materials are suited for this purpose, the examples being barium sulfate, silicon carbide, silicon nitride, alumina and zirconia. The mixing ratio of the X-ray radioopaque material may be selected depending on the desired X-ray shielding effect, and in general the aforementioned non-magnetic and X-ray radioopaque material is dispersed in the vessel in a mixing ratio of from 10 to 45 wt % so that the image of the skin marker of the invention can be clearly discriminated from those of the soft tissues of the living body.

It is found that some of the commercially available catheters for the X-ray angiography are made of plastics containing X-ray radioopaque materials, typically barium sulfate. Such catheter may be conveniently used in the present invention as the vessel for containing the aqueous solution of polyvinyl alcohol after closing one end of the tubular catheter. However, it should be noted here that if the catheters commercially sold for the X-ray angiography contain magnetic materials, the NMR system is adversely affected by the magnetic materials. It is, therefore, necessary to ascertain that the selected catheter does not influence the NMR-CT image adversely, prior to practical use thereof in the present invention.

In the present invention, a specifically defined polyvinyl alcohol is used as the gel component to form the hydrogel having the required characteristics. However, the hydrogel may be added with an additive which neither hinders gelation of the polyvinyl alcohol nor attenuates the proton NMR signal emitted from the hydrogel. The amount of such additive may be up to $\frac{1}{2}$ of the weight of the polyvinyl alcohol.

Examples of the additive which neither hinders gelation of the polyvinyl alcohol nor attenuates the proton NMR signal emitted from the hydrogel, are lecithin, vegetable oils, animal oils, glucose, casein, iodine, methyl alcohol, propyl alcohol and butyl p-hydroxybenzoate. One or a mixture of them may be added to the aqueous solution of polyvinyl alcohol directly or in the form of an aqueous solution or suspension, and then dispersed uniformly by agitation, the aqueous solution of polyvinyl alcohol being thereafter subjected to the aforementioned cyclic operations of freezing and thawing.

The presence of a trace amount of a paramagnetic substance, such as nickel, vanadyl, iron (III), dysprosium, cobalt and gadolinium, is rather preferred, since the longitudinal relaxation time $T_1$ of proton in the high water content hydrogel is extremely decreased particularly when compared with the transverse relaxation time $T_2$ so that the NMR signal from the hydrogel is markedly intensified. The skin marker of the invention containing the paramagnetic substance gives a distinctively clear image by the NMR-CT. The optimum concentration in the hydrogel of the paramagnetic substances is as follows: 10 to 350 mM/l (0.06 to 2.1%) for the cobalt ion, 0.1 to 350 mM/l (6ppm to 5.7%) for the vanadyl, dysprosium and nickel ions, 0.1 to 10 mM/l (6 to 635 ppm) for the copper ion, and 0.05 to 3.5 mM/l (3 to 550 ppm) for the ferric and gadolinium ions. The transverse relaxation time $T_2$ of the proton in the hydrogel is shortened to depress the effect of increasing the NMR signal as the amount of the co-existing paramagnetic substance is increased further beyond the range as described above, it is preferable that the added amount thereof be controlled in the aforementioned optimum range.

The water content of the hydrogel in the skin marker, according to this invention, may range within 80 to 92 wt %. Although the content of water in the resultant hydrogel depends upon the formulation of the initially prepared aqueous solution or suspension of polyvinyl alcohol, the aqueous solution or suspension of polyvinyl alcohol is gelled to form the hydrogel of final state without appreciable change in water content, so that the water content of the hydrogel at the final stage may be easily calculated and controlled.

A hydrogel having a water content of less than 80%, for instance 30 to 79%, may be prepared by suitably adjusting the composition of the aqueous polyvinyl solution or suspension used at the initial step. However, in consideration of the aimed use, i.e. application thereof as a skin marker, a hydrogel having a water content of about 73% gives an NMR signal substantially equivalent to that emitted from the liver, and the signal intensity of a hydrogel having a water content of 75% is weaker than that emitted from the cerebral grey matter while it gives an image clearer than that of the liver. In order to ensure that the intensity of NMR signal emitted from the hydrogel is comparable to those from the cerebral white matter and fats, it is preferable that the water content of hydrogel is within the defined range of from 80 to 92%. It is more preferred, for obtaining an image clearer than those of the living tissues, that paramagnetic substances, such as nickel, copper, vanadyl, iron, dysprosium, cobalt, or gadolinium be present in the hydrogel.

The skin marker of the invention emits an intense NMR signal to be imaged clearly by the NMR-CT system, and at the same time an X-ray tomograph is distinguished readily from those of the soft living tissues, hypodermal fat layer and skin since the vessel per se containing the high water content hydrogel does not have radiolucency against X-ray. Accordingly, the skin marker of the invention can be used both for the NMR-CT and X-ray tomograph systems for the precise determination of steric interrelation between certain position or positions on the skin and the internal lesion site during the clinical diagnoses.

The skin marker of the invention may be cut to have an appropriate shape and dimensions by scissors or other means in conformity with the requirements in the actual diagnostic treatments, the extent and shape of the lesion being the major factors for such requirements.

Although the skin marker of the invention contains a large amount of water, it has satisfactory shape retaining property at 37° C., the normal stem temperature, whereby the skin marker of the invention has a superior advantage that the content in the vessel does not leak out. In connection with this advantage or merit, it should be noted here that the conventional materials, e.g. vegetable, animal and silicone oils, filled in the vessel for the marking purpose tend to flow out of the vessel particularly when the conventional skin marker is cut.

The skin marker of the invention may be stored in a simple manner, without changing its condition of retaining a large amount of water for a storage period of longer than a half year or more when stored in a sealed container, and emits an intense NMR signal clearly different from that emitted from the skin of living body in addition to the X-ray radioopaque property.

Since the skin marker of the invention does not contain magnetic substances including ferromagnetic materials represented by iron, cobalt, nickel, chromium halides and chromium oxide, and ferrimagnetic substances represented by nickel(II) iron(III) oxide, iron(III) iron-(II) oxide, manganese(II) iron(III) oxide, γ-iron(III) oxide, nickel zinc ferrite and manganese zinc ferrite, it does never cause malfunction or other hindrance of the operations of the NMR-CT system.

EXAMPLES OF THE INVENTION

The present invention will now be described in detail while referring to Examples and Comparative Example. In the following Examples and Comparative Example, "%" and "ppm" stand for "% by weight" and "ppm by weight".

EXAMPLE 1

314g of a 20% aqueous solution of a polyvinyl alcohol having an average polymerization degree of 1,000 and a degree of hydrolysis of 98 mol % was put into a disk-form vessel II (see FIG. 1) (made of a polyethylene dispersed with 45% of barium sulfate and having a depth of 3 mm, a diameter of 2 cm and a wall thickness of 0.7 mm), and then cooled to −(minus) 30° C. to prepare a frozen mass which was subjected to thawing operation. The cycle of alternate freezing and thawing operations was repeated to form a generally disk-shaped composite product 10 comprising the vessel 11 and a hydrogel 12 contained therein adapted for use as a skin marker 10, as shown in FIG. 1.

The thus formed skin marker 10 was placed in an NMR-CT system (0.15T, 6.3 MHz), and the proton longitudinal relaxation time $T_1$ and the proton transverse relaxation time $T_2$ thereof were measured to find $T_1 = 0.35$ sec and $T_2 = 0.15$ sec. The intensity I of the NMR signal was calculated from the following equation (1).

$$I = k \cdot \rho \exp(-2\tau/T_2)[1 - \exp(-Tr/T_1)] \quad (1)$$

wherein k is a constant, $\rho$ is the density of proton, $2\tau$ is the echo time (48 milliseconds), and Tr is the pulse repetition time (500 milliseconds). Similarly, the intensity of the NMR signal from the liver was calculated while substituting the proton relaxation times $T_1 = 0.3$ sec, $T_2 = 0.05$ sec for the $T_1$ and $T_2$ in the equation (1). By comparing the calculated results, it was estimated that the intensity of the signal emitted from the skin marker 10 of the invention is about 1.3 times as high as that of the liver. In fact, the small disk-shaped composite product, i.e. a skin marker 10 of this invention, was applied on the skin of the front chest of a volunteer while supposing the case for finding out the precise steric position on which a radiation should be focused, and an NMR tomographic picture was taken both through the marker 10 and the liver (imaginal lesion site) under the conditions that the static magnetic field intensity was 0.15T, the pulse interval was 500 milliseconds and the echo time was 48 milliseconds. The result was that both of the skin marker 10 and the liver were imaged, with the surface of the skin being not imaged, and the image of the marker 10 of the invention was clearer than that of the liver. With reference to the thus taken NMR tomographical picture, it had been made possible to seize easily the steric interrelation between the location on the skin applied with the skin marker 10 and the local part of the liver. The marginal portions of the skin marker 10 could be cut in a simple manner using scissors in conformity with the shape of the local part of liver (imaginal lesion site) while photographing the sectional images of the marker 10 and the liver along various directions, without suffering from the inconvenience that any liquid ingredient flowed out from the cut position. Then, without removing the marker 10, X-ray-CT images of the chest and abdomen of the volunteer were taken to ascertain that the envelope or vessel portion of the marker 10 was clearly discriminated as forming an image of the portion through which X-ray had not been passed.

After removing the marker 10 and then stored for six months in the sealed condition, $T_1$ and $T_2$ of the marker 10 were measured again to obtain the results of $T_1 = 0.34$ sec and $T_2 = 0.15$ sec, the results being substantially equal to those at the time immediately after the preparation thereof. The same marker 10 was applied on the skin of the chest of the volunteer and another examination was conducted generally similarly to the preceding procedures, whereby an NMR signal which was more powerful than that emitted from the liver was recognized. From this result, together with the result that the marker 10 was clearly discriminated as forming an image of radioopaque portion through the X-ray-CT, it was found that the skin marker had the utilities both in the NMR-CT and the X-ray-CT systems.

EXAMPLE 2

Figure 2:
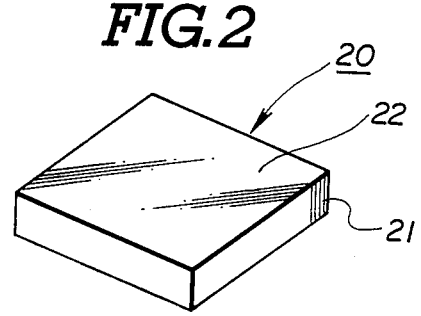
FIG. 2 is a perspective view illustrating another skin marker embodiment as made in Example 2.

A 15% aqueous solution of a polyvinyl alcohol having an average polymerization degree of 2,000 and a degree of hydrolysis of 99 mol % was cast in a 25 mm × 25 mm × 3 mm container 21 (see FIG. 2) (having a wall thickness of 1 mm, and made of a polyvinylchloride dispersed with 15% of silicon carbide), and then subjected to two cycles of freezing and thawing operations, whereby a high water content hydrogel 22 containing 85% of water was prepared. The NMR characteristics of the thus prepared hydrogel marker 20 shown in FIG. 2 were measured using the same NMR system as used in Example 1 to obtain the results of $T_1 = 0.53$ sec and $T_2 = 0.22$ sec. These results were substituted in the equation (1) as set forth in Example 1 to calculate the NMR signal intensity of the marker 20. The calculation revealed that the NMR signal was clearer than that of the intestines ($T_1 = 0.4$ sec, $T_2 = 0.07$ sec.) with the estimated signal intensity ratio being 1.2 to 1.3. The skin marker 20 was applied on the skin of the front chest of a volunteer and an NMR tomographic image and images of the chest and abdomen were photographed through both of the marker 20 and the middle lobe. The results were that the middle lobe, the larger intestine and the small intestine were imaged with the image of the marker while the skin surface per se was not imaged, with the image of the marker 20 of the invention being clearer than those of the middle lobe, the larger intestine and the small intestine. Then, without removing the marker 20, X-ray-CT images were photographed to find that the envelope or container of the skin marker 20 was clearly discriminated.

EXAMPLE 3

Figure 3:
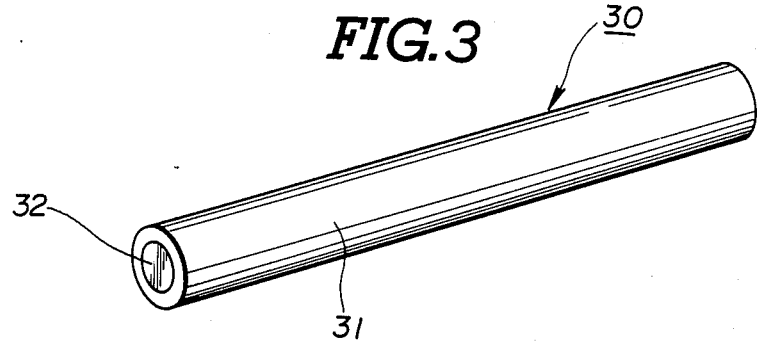
FIG. 3 is a perspective view illustrating still another skin marker embodiment as made in Example 3.

Into a 15% aqueous solution of a polyvinyl alcohol having an average polymerization degree of 2,600 and a degree of hydrolysis of 99 mol %, nickel chloride hexahydrate was dissolved so that the concentration of the nickel chloride was 0.28% which corresponded to 700 ppm (12 mM/l) for the concentration of nickel ion. Separately prepared were a glass test tube having an inner diameter of 22 mm and a length of 20 cm, and a commercially sold catheter 31 (see FIG. 3) for the blood angiography having an inner diameter of 1.8 mm, an outer diameter of 2.35 mm and a length of 20 feet (6 meters) and made of polyethylene dispersed with 40% of an X-ray shielding agent (barium sulfate). Both of the containers were filled with the aforementioned aqueous solution containing the polyvinyl alcohol and the nickel ions, and the ends of the catheter were tied up. The contents in both containers were frozen and then thawed for two times. Then, the catheter 31 was cut into segments as shown in FIG. 3 each having a length of 35 cm, to find that the contents 32 therein did not flow out.

The high water content hydrogel was removed from the glass test tube, and the relaxation times thereof were measured using the same NMR system as used in Example 1 to find $T_1 = 109$ to 133 milliseconds and $T_2 = 106$ to 114 milliseconds. Irrespective of the fact that the longitudinal relaxation time $T_1$ was decreased to about 1/4 to 1/5 as compared with the case of Example 2 wherein the hydrogel was prepared from a 15% aqueous solution of polyvinyl alcohol without added with nickel ions and having the relaxation times of $T_1 = 500$ milliseconds and $T_2 = 220$ milliseconds, the decrease in transverse relaxation time $T_2$ in this Example was only 1/2. In view of this result, it was expected from the calculation through the equation (1) that the proton NMR signal intensity of the hydrogel was enhanced by about 1.2 times by the addition of nickel ions so that the final signal intensity reached about 1.4 times as high as that of cerebral white matter ($T_1 = 300$ milliseconds, $T_2 = 80$ milliseconds). The cut segments of the skin marker 30 prepared from the aforementioned polyethylene catheter 31 were applied and fixed on the left and right temples and occipital region of a patient who had a cancer at the meso-pharyngis, and X-ray-CT tomograph was taken, whereby the images of the catherters, conventionally used for blood angiography and filled with the hydrogel of the invention in this Example, and the image of a tumor at the right pharyngis were found and the precise steric interrelation between the lesion and the locations applied with the catheters was determined.

Without removing the catheters or skin markers 30, NMR-CT pictures were taken subsequently to find discriminative images of the skin markers (catheters) in both of the picture bearing the images of transverse sections and the picture bearing the images of the coronal sections.

The same skin markers 30 were applied on the occipital region, the nucha and the lower abdomen, respectively, and NMR-CT pictures were inspected. The results were that the markers 30 were imaged clearer than those of the liver, kidney, pancreas, spleen, lungs, urinary bladder, cerebral white matter and fat layers in all cases.

EXAMPLE 4

The aqueous solution prepared in Example 3 and containing the polyvinyl alcohol and nickel ions was filled in a tube (made of polyethylene dispersed with 15 wt % of silicon carbide acting as an X-ray shielding agent) having an inner diameter of 3.3 mm, an outer diameter of 3.8 mm and a length of 20 cm, and a hydrogel was prepared generally following the procedures as described in Example 3.

The thus fabricated skin markers were applied on the surface of the chest and upper abdomen of a patient. Images of the skin markers were discretely observed in the NMR-CT pictures. Without removing the skin markers, X-ray-CT pictures were taken to find that the skin markers were clearly imaged to show the skin portions which did not transmit X-ray.

On the other hand, the skin markers (prepared from a commercially sold catheter having an inner diameter of 1.8 mm) prepared in Example 3 were applied on the chest and upper abdomen of a patient who was then subjected to photographing through an NMR-CT system. The images of the markers could not be distinctively appreciated. The result may be interpreted that the skin markers each having a small inner diameter of only 1.8 mm did not give appreciable images since no synchronized photographing system was used for synchronizing with the breathing and pulsation of the heart in the experiment although the skin surfaces at the chest and upper abdomen were moved by the breathing and pulsation as well known in the art. As has been described hereinbefore, a skin marker having an inner diameter of 3.3 mm was appreciable with satisfactory clearness.

COMPARATIVE EXAMPLE 1

Into the same commercially sold catheter as used in Example 3, filled was a silcone oil ($T_1 = 418$ milliseconds, $T_2 = 469$ milliseconds) which had been used as a conventional skin marker agent in the NMR-CT. After sealing the ends of the catheters, each of the catheters was applied on the occipital region and then imaged by an NMR-CT system. The image thereof had a high luminance equivalent to or somewhat superior over that of cerebral white matter. However, during the continued imaging operations along varied directions while using the cut catheter segments each having a desired length of about 30 cm, silicone oil flowed out from the cut sections of the catheters.

In order to obviate the inconvenience or defect of the silicone oil, the same catheter was filled, respectively, with agar ($T_1 = 0.5$ to 2 sec, $T_2 = 0.005$ to 0.006 sec), KONNYAKU (devil's tongue, $T_1 = 1.4$ sec, $T_2 = 0.07$ sec), boiled egg (the yolk, $T_1 = 0.06$ sec, $T_2 = 0.06$ sec), gelatine ($T_1 = 0.2$ sec, $T_2 = 0.12$ sec) and polyacrylamide gel ($T_1 = 0.2$ to 2 sec, $T_2 = 0.08$ to 1 sec).

However, the intensity of NMR signal emitted from the agar was extremely feeble, as will be apparent from the fact that the value of $T_2$ is so short as compared with that of $T_1$. Although the intensities of signals emitted from the KONNYAKU, boiled egg, gelatine and polyacrylamide gel were relatively higher than that emitted from the agar, those signals were substantially equivalent to that emitted from the cerebral white matter. In addition, extreme difficulties were encountered in filling the KONNYAKU, boiled egg and polyacrylamide gel into the tubes such that a large amount of air bubbles was formed in each of the mass filled by ordinary filling technique. It was thus concluded that these materials were disadvantageous for use in production of skin markers. The gelatine could be relatively easily filled in a tube since an aqueous solution of gelatine was cast in the tube followed by cooling to form a gel. However, the thus formed gelatine gel was changed to a viscous liquid at a temperature of 20° to 25° C. and leaked from the tube similarly to the silicone oil.

Although the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A process for making a skin marker for diagnosis by X-ray tomography and nuclear magnetic resonance imaging, comprising a casting step of casting into a vessel an aqueous solution containing more than 8 wt % and not more than 20 wt % of a polyvinyl alcohol having a degree of hydrolysis of not less than 98 mol % and an average polymerization degree of not less than 1,000, a non-magnetic and X-ray radioopaque material being dispersed in a wall of said vessel, a freezing step of cooling the cast aqueous solution of to a temperature of not higher than −(minus) 10° C. to obtain a frozen mass and a thawing step of thawing said frozen mass to obtain a hydrogel of high water content filled in said vessel.

2. The skin marker process according to claim 1, wherein said vessel is made of a material to be easily cut, said material being selected from the group consisting of synthetic resins and natural and synthetic rubbers.

3. The skin marker process according to claim 2, wherein said synthetic resin is selected from the group consisting of polyethylene, polypropylene, polyamides, polyvinylchloride, polyvinylidene chloride, polyesters, polyacrylonitrile, polyfluoroethylene, and silicon resins.

4. The skin marker process according to claim 1, wherein said non-magnetic and X-ray radioopaque material is dispersed in said vessel in a mixing ratio of from 10 to 45 wt %.

5. The skin marker process according to claim 1, wherein said non-magnetic and X-ray radioopaque material is selected from the group consisting of barium sulfate, silicon carbide, silicon nitride, alumina and zirconia.

6. The skin marker process according to claim 1, wherein said hydrogel is added with an additive which neither hinders gelation of said polyvinyl alcohol nor attenuates the proton NMR signal emitted from said hydrogel.

7. The skin marker process according to claim 6, wherein said additive is added in an amount of not more than $\frac{1}{2}$ of the weight of said hydrogel.

8. The skin marker process according to claim 6, wherein said additive is selected from the group consisting of lecithin, iodine, vegetable oils, animal oils, glucose, casein, methyl alcohol, propyl alcohol and butyl p-hydroxybenzoate.

9. The skin marker process according to claim 6, wherein said additive is selected from the group consisting of nickel, vanadyl, iron (III), dysprosium, cobalt and gadolinium.

10. The skin marker process according to claim 1, wherein said hydrogel has a water content of from 80 to 92 wt %.

11. The skin marker process according to claim 1, wherein said process further comprises, after said thawing step, one to seven additional cyclic processing steps each including said freezing and thawing steps.

* * * * *